United States Patent [19]

Permenter

[11] Plant 4,086

[45] Aug. 2, 1977

[54] ROSE PLANT

[75] Inventor: Ethel J. Permenter, Los Alamitos, Calif.

[73] Assignee: Jackson & Perkins Co., Medford, Oreg.

[21] Appl. No.: 722,714

[22] Filed: Sept. 13, 1976

[51] Int. Cl.[2] ..... A01H 5/00

[52] U.S. Cl. ..... Plt./15

[58] Field of Search ..... Plt./15

*Primary Examiner*—Robert E. Bagwill

*Attorney, Agent, or Firm*—Klarquist, Sparkman, Campbell, Leigh, Hall & Whinston

[57] ABSTRACT

This novel rose variety is a mutation of Medallion, and differs therefrom by its blossom colors, which lack the cinnamon shadings of the parent variety.

1 Drawing Figure

1

The present invention relates to a new and distinct variety of rose plant of the hybrid tea class, which was discovered by me as a cultivated sport of the hybrid tea rose Medallion, (U.S. Plant Pat. No. 2,997), said discovery having been made in a plant grown by me at Los Alamitos, Calif.

On the Medallion rose bush grown by me, I discovered that flowers on one of the branches were distinctly different from a normal Medallion in that they were more yellow from bud to open flower and lacked the cinnamon shade that normally is possessed by the Medallion cultivar. Propagation of the budding eyes of this one stem proved that this sport came through in successive propagations.

This new cultivar is substantially identical in all respects to its parent, except for the difference in bud and blossom color noted above. The attached drawing shows the stem leaves and blossom stages of the new cultivar (identified as S-238) and the normal blossom and buds of the Medallion cultivar.

As observed at Irvine, Calif., the new rose variety had

2 blossom coloration in accordance with *Color Standards and Nomenclature,* Ridgeway, as noted below:

Bud:

*Size.*—Very large.

*Color.*—Antimony yellow, Pl. 15, 17′ — b.

Bloom:

*Color.*—Half open: upper side — pale yellow orange, Pl. 3, 15 — f; reverse side — pale yellow orange, Pl. 3, 15 — f; full open: upper side — apricot yellow, Pl. 4, 19 — b; reverse side — apricot yellow, Pl. 4, 19 — b.

Being substantially identical to the parent variety except for the aforementioned distinctions, reference is made to U.S. Plant Pat. No. 2,997 for further description of this variety.

I claim:

1. A new and distinct variety of rose plant of the hybrid tea class, substantially as herein shown and described, characterized particularly as to novelty by the generally yellow color of bud and bloom on a plant otherwise identical to the variety Medallion.

* * * * *

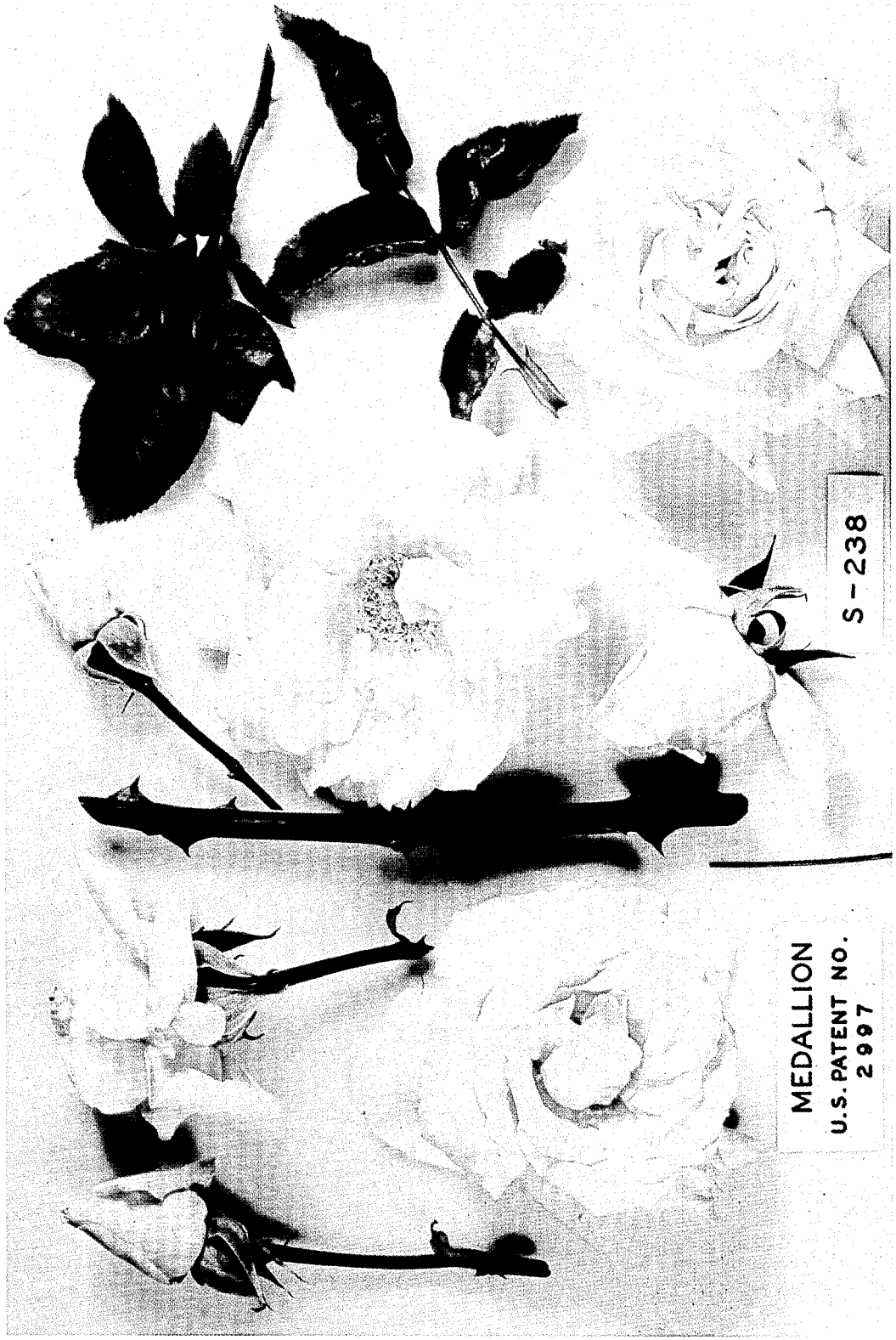
S-238
MEDALLION
U.S. PATENT NO.
2997